United States Patent
Wang

(10) Patent No.: US 6,290,722 B1
(45) Date of Patent: Sep. 18, 2001

(54) TACKY ATTACHMENT METHOD OF COVERED MATERIALS ON STENTS

(75) Inventor: Chicheng Wang, Sunnyvale, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

(21) Appl. No.: 09/523,635

(22) Filed: Mar. 13, 2000

(51) Int. Cl.[7] ............................................. A61F 2/04
(52) U.S. Cl. ................................. 623/1.46; 623/1.44
(58) Field of Search ..................... 623/1.13, 1.46–1.48, 623/1.45, 1.44; 606/194; 604/104

(56) References Cited

U.S. PATENT DOCUMENTS

| | | | |
|---|---|---|---|
| 5,421,955 | 6/1995 | Lau et al. | 216/48 |
| 5,514,154 | 5/1996 | Lau et al. | 606/195 |
| 5,569,295 | 10/1996 | Lam | 606/198 |
| 5,593,434 | 1/1997 | Williams | 623/1 |
| 5,603,721 | 2/1997 | Lau et al. | 606/195 |
| 5,618,299 | 4/1997 | Khosravi et al. | 606/198 |
| 5,637,113 | 6/1997 | Tartaglia et al. | 623/1 |
| 5,649,952 | 7/1997 | Lam | 606/198 |
| 5,693,085 * | 12/1997 | Buirge et al. | 606/194 |
| 5,700,286 * | 12/1997 | Tartaglia et al. | 604/104 |
| 5,725,572 | 3/1998 | Lam et al. | 623/1 |
| 5,728,158 | 3/1998 | Lau et al. | 632/12 |
| 5,735,893 | 4/1998 | Lau et al. | 623/1 |
| 5,759,192 | 6/1998 | Saunders | 606/194 |
| 5,766,238 | 6/1998 | Lau et al. | 623/1 |
| 5,843,172 | 12/1998 | Yan | 623/1 |
| 5,849,037 | 12/1998 | Frid | 623/1 |
| 5,876,432 | 3/1999 | Lau et al. | 623/1 |
| 5,891,191 | 4/1999 | Stinson | 623/1 |
| 5,897,911 | 4/1999 | Loeffler | 427/2.25 |

* cited by examiner

*Primary Examiner*—Cary E. O'Connor
(74) *Attorney, Agent, or Firm*—Schwegman, Lundberg, Woessner & Kluth, P.A.

(57) ABSTRACT

The present invention includes a stent. The stent comprises a structural support and a polymeric film or sheet or tube that overlays the structural support. The stent also includes a tacky portion that adheres the polymeric film or sheet or tube to the structural support. The tacky portion comprises sugar or starch or polyvinylalcohol or degradation products of these materials.

18 Claims, 6 Drawing Sheets

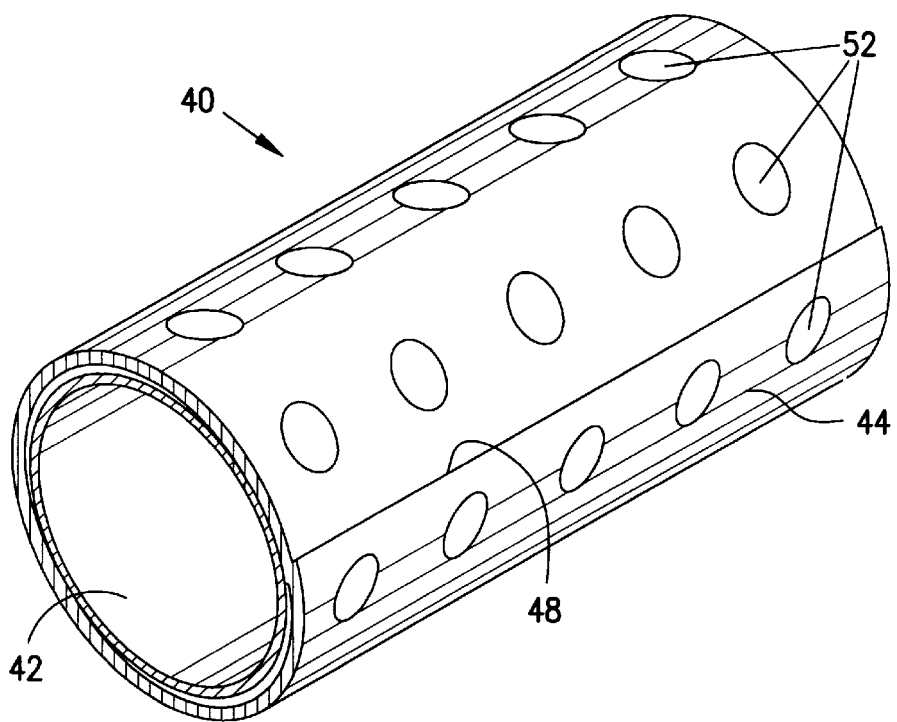
FIG. 5
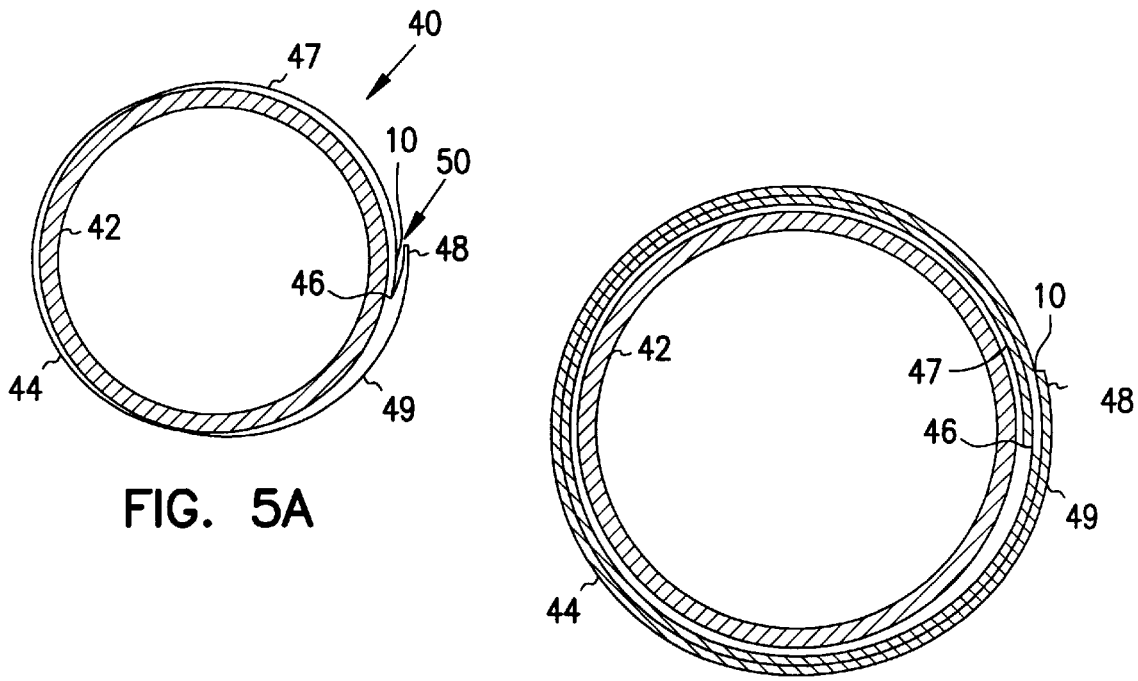
FIG. 5A
FIG. 5B

TACKY ATTACHMENT METHOD OF COVERED MATERIALS ON STENTS

BACKGROUND OF THE INVENTION

The present invention relates to a tacky attachment for adhering a cover to a stent and to a method for adhering a cover to a stent.

Stents are typically implanted within a vessel in a contracted state and expanded when in place in the vessel in order to maintain patency of the vessel to allow fluid flow through the vessel. Implantation of stents is typically accomplished by mounting the stent on a balloon portion of a catheter, positioning the stent in a body lumen and expanding the stent to an expanded state by inflation of a balloon within the stent. The stent is left in place by deflating the balloon and removing the catheter.

Stents typically have a metallic structure to provide strength which is required to function or to support a stent. However, metals do not provide for delivery of localized therapeutic pharmacological treatment of a vessel at the location being treated within the stent.

Polymeric materials capable of absorbing and releasing therapeutic agents typically do not fulfill structural and mechanical requirements of a stent, especially when the polymeric materials are loaded with a drug, since the drug loading of a polymeric material significantly affects the structural and mechanical properties of the polymeric material.

U.S. Pat. No. 5,637,113, which issued Jun. 10, 1997, to Tarataglia et al. describes a metallic stent which is wrapped with a polymer film. The polymer film is capable of carrying and releasing therapeutic agents. The polymeric film is secured to the metallic stent by a mechanism such as an adhesive bonding. The adhesive is a copolymer of poly-L-lactic acid (L-PLA) and polycaprolactone (PCL). Other adhesives, heat bonding, solvent bonding and one or more mechanical fasteners, such as a metal clip are also suitable.

SUMMARY OF THE INVENTION

One embodiment of the present invention includes a stent. The stent comprises a structural support. A polymeric film or sheet or tube overlays the structural support. A tacky portion adheres the polymeric film to the structural support. The tacky portion comprises sugar or starch or polyvinylalcohol or degradation products or mixtures of these materials.

Another embodiment of the present invention includes an adhering system. The adhering system comprises a tacky material or a mixture of tacky materials. The tacky materials include sugar, starch or polyvinylalcohol or degradations products or mixtures of these materials.

One other embodiment of the present invention includes a method for adhering a polymeric sheet or tube to a stent structural member. The method includes providing a stent structural member and providing a polymeric sheet or tube. The method also includes preparing a mixture comprising sugar, polyvinylalcohol, starch or a mixture or degradation products of sugar, polyvinylalcohol or starch and a solvent. The mixture is applied to either the stent structural member or the polymeric sheet or tube.

Another embodiment of the present invention includes a stent assembly. The stent assembly comprises a structural member, a polymeric sleeve and a tacky portion. The tacky portion adheres the sleeve to the structural member. The tacky portion comprises one or more of a sugar, a starch, polyvinylalcohol or a mixture of these materials or degradation products of these materials.

Another stent assembly embodiment of the present invention comprises a structural member, a polymeric sheet and a tacky portion. The tacky portion adheres the polymeric sheet to the structural member and adheres one end of the sheet to the sheet to form a sheet tube. The tacky portion comprises one or more of a sugar, a starch, polyvinylalcohol or a mixture of these materials or degradation products of these materials.

DESCRIPTION OF THE DRAWINGS

FIG. 5 illustrates a perspective view of one embodiment of a stent-tacky layer-polymeric cover wherein the polymeric cover is drug loaded.

FIG. 5A illustrates in cross-section the stent-tacky layer-polymeric cover of FIG. 5 in an unexpanded position.

FIG. 5B illustrates in cross-section the stent-tacky layer-polymeric cover of FIG. 5 in an expanded position.

DETAILED DESCRIPTION

Figure 1:
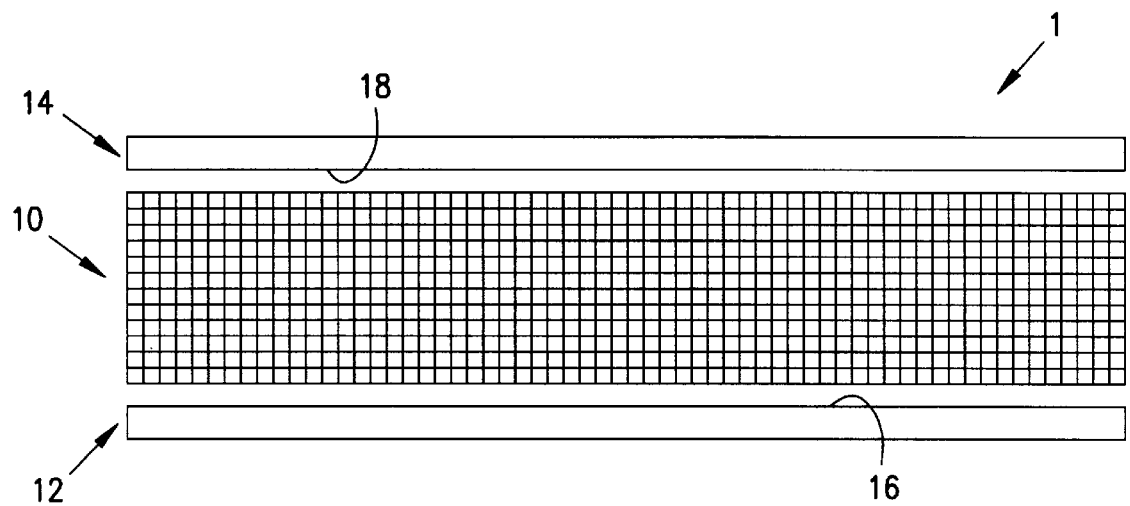
FIG. 1 illustrates a cross-sectional view of the tacky layer of the present invention sandwiched between a stent and a polymeric cover.
Figure 2:
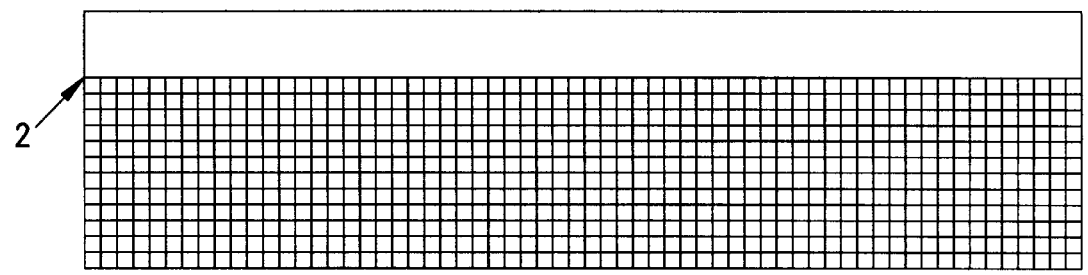
FIG. 2 illustrates a cross-sectional view of the tacky layer of the present invention adhered to a polymeric cover.

One embodiment of a stent assembly the present invention comprises a tacky layer 10 which is sandwiched between a stent 12 and a cover 14, as is illustrated generally at 1 in FIG. 1. The tacky layer 10 is applied to either an outer surface 16 of stent 12 or to an inner surface 18 of cover 14. After the tacky material is applied to form the tacky sandwich layer 10 between the stent 12 and polymeric cover 14, the stent 12 and polymeric cover material 14 are subjected to a heat and temperature that form a physical bond, as is shown generally at 2 in FIG. 2. The physical bond has a predetermined adherent strength and quality which prevents the polymeric cover material 14 from detaching from the stent 12 during delivery of the stent and deployment of the stent 12 relative to a lesion while maintaining adhesion during expansion of the stent 12 and polymeric cover 14.

The tacky layer 10 is implantable and biodegradable. The tackiness of the tacky layer 10 is adjustable by selecting an appropriate base material. The base material is selected to impart a "sticky" quality to the layer 10 and to adhere the stent 12 and polymeric cover material 14 to each other. Specific examples of base materials used in the present invention include sugars such as monosaccharides, disaccharides, polysaccharides, or mixtures of these sugars or their degradation products. Examples of specific sugars that can be used to make the tacky layer include pentoses such as xylose, arabinose, and fructose; hexoses and disaccharides such as galactose, sorbose, sucrose, maltose; or polysaccharides such as starch and cellulose or earboxymethyl cellulose, maltodextrin and polyvinyl alcohol (PVA). Embodiments of the tacky layer base material also include mixtures of these materials and degradation products of these materials.

The sugar, starch, polyvinyl alcohol or mixtures or degradation products of these materials are mixed with water and are uniformly applied, in one embodiment, to an outer surface of the stent to form the tacky layer. The tacky layer is applied substantially uniformly to the stent. For some embodiments, the sugar, starch, polyvinyl alcohol or mixture of these materials are mixed with another solvent, such as glycerine. The solvent is biocompatible and has no adverse environmental effects.

The tacky materials are applied to the stent 12 or, for some embodiments, the polymeric cover surface 18 by mechanisms that include spreading or spraying at room temperature or spraying at elevated temperatures. The stent 12 and polymeric cover materials 14 are then physically bonded to each other at room temperature for some embodiments and at an elevated temperature for other embodiments, by the tacky layer.

The temperature range to which the coated stent is subjected is about room temperature to about 100 degrees Centigrade. The pressure range to which the coated stent is subjected is about 50 psi to 250 psi. When subjected to these temperatures and pressures, the tacky layer of the present invention 10 is imparted with adhesive properties that physically bind the polymeric cover 14 to the stent 12. The tacky layer 10 has a deformability that maintains the physical bond between the stent and the polymeric cover while the stent and polymeric cover are expanded in situ.

Figure 3:
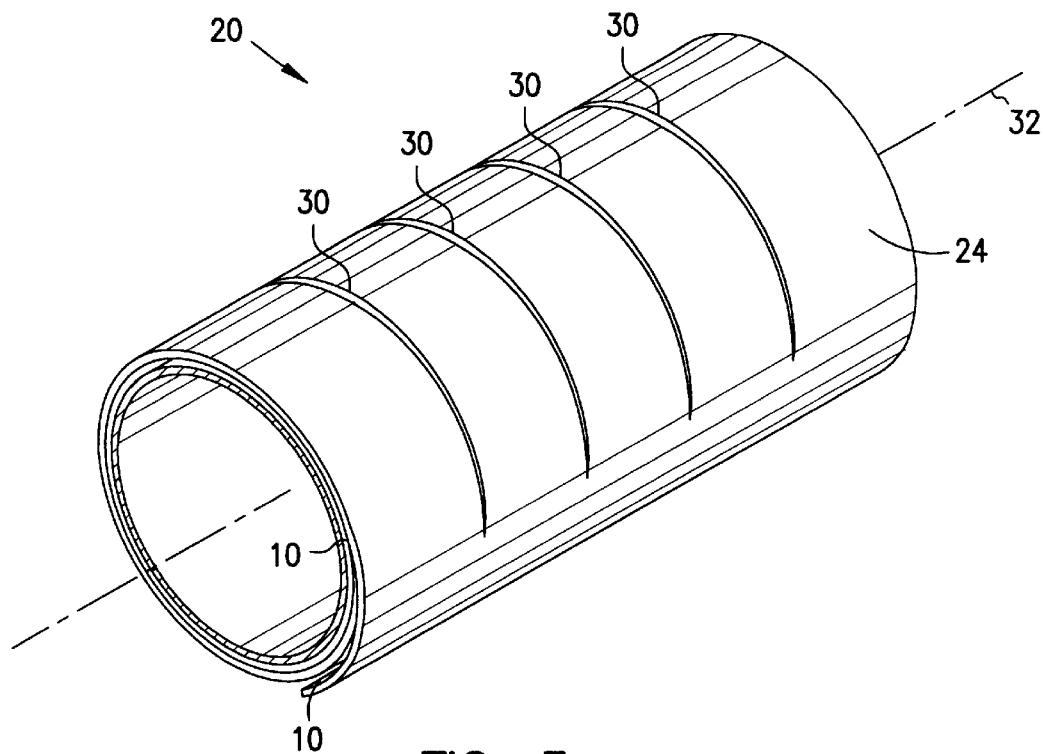
FIG. 3 illustrates a perspective view of one embodiment of an expandable stent-tacky layer-polymeric cover of the present invention.

One stent embodiment of the present invention, illustrated generally at 20 in FIG. 3, comprises an expandable stent structural member 22 and a planar sheet or film 24 of polymeric material. The structural member 22 is shown in an unexpanded state in cross-section in FIG. 3A and in an expanded state in FIG. 3B. In a first embodiment, the polymeric planar sheet or film 24 is attached to the stent member 22, which is metal, at one or more points of attachment 26. The attachment occurs through use of the tacky layer of the present invention.

Figure 3A:
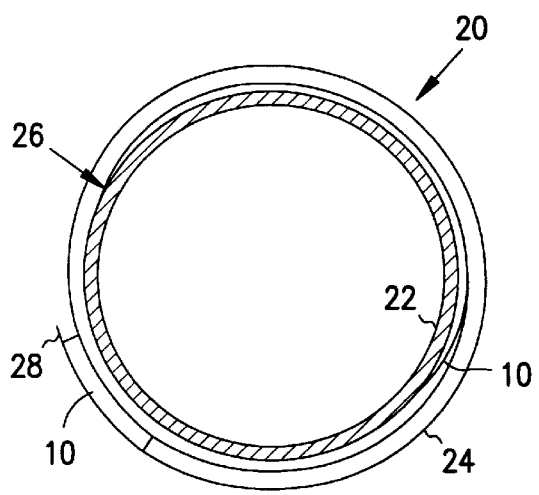
FIG. 3A illustrates in cross-section the expandable stent-tacky layer-polymeric cover of the present invention in an unexpanded position.
Figure 3B:
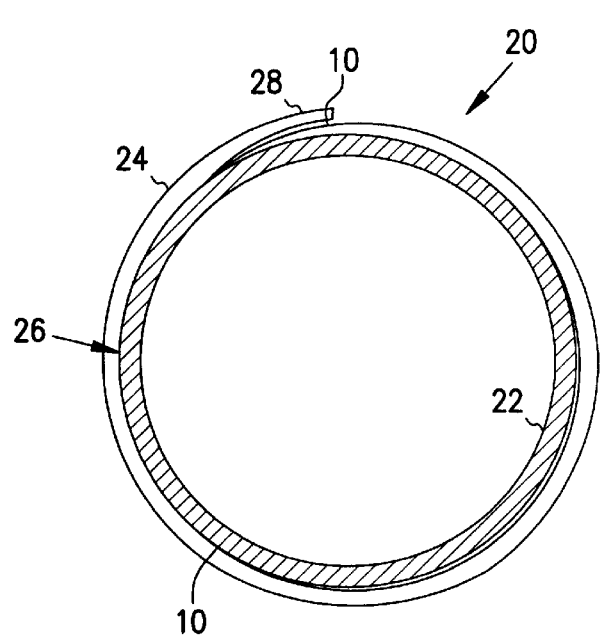
FIG. 3B illustrates in cross-section the expandable stent-tacky layer-polymeric cover of the present invention in an expanded position.

The film or planar sheet 24 has a free end and for some embodiments, defines one or more slits 30 in the polymeric film transverse to the axis 32 of the stent in order to accommodate possible uneven expansion of the stent structural member 22. The planar sheet of polymeric material 24 is adapted to uncoil and to expand in order to match expansion of the stent structural member 22. In particular, a strip of an inside surface of the polymeric film 24 is coated with the tacky layer 10 in order to adhere an end 28 of the polymeric sheet to the rolled sheet 24 as shown in FIGS. 3, 3A and 3B.

Figure 4:
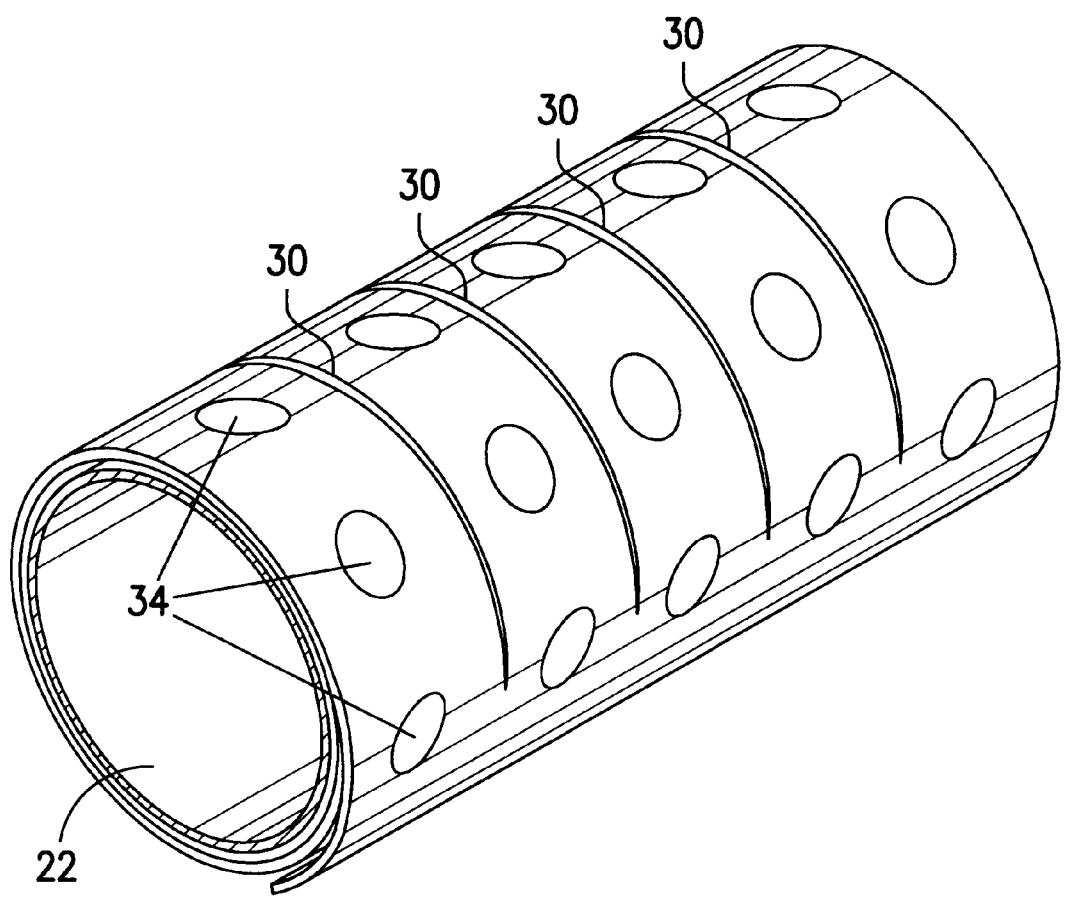
FIG. 4 illustrates a perspective view of one embodiment of an expandable stent-tacky layer-polymeric cover wherein the stent and polymeric cover define apertures.

The planar sheet of polymer material 24 is a solid sheet for some embodiments but for other embodiments, the sheet includes a surface that defines a plurality of apertures 34 of various sizes and shapes in order to promote rapid endothelialization, such as is illustrated in FIG. 4. The stent is mountable on a balloon dilatation catheter for deployment of the stent in the vasculature of a patient.

Figure 7A:
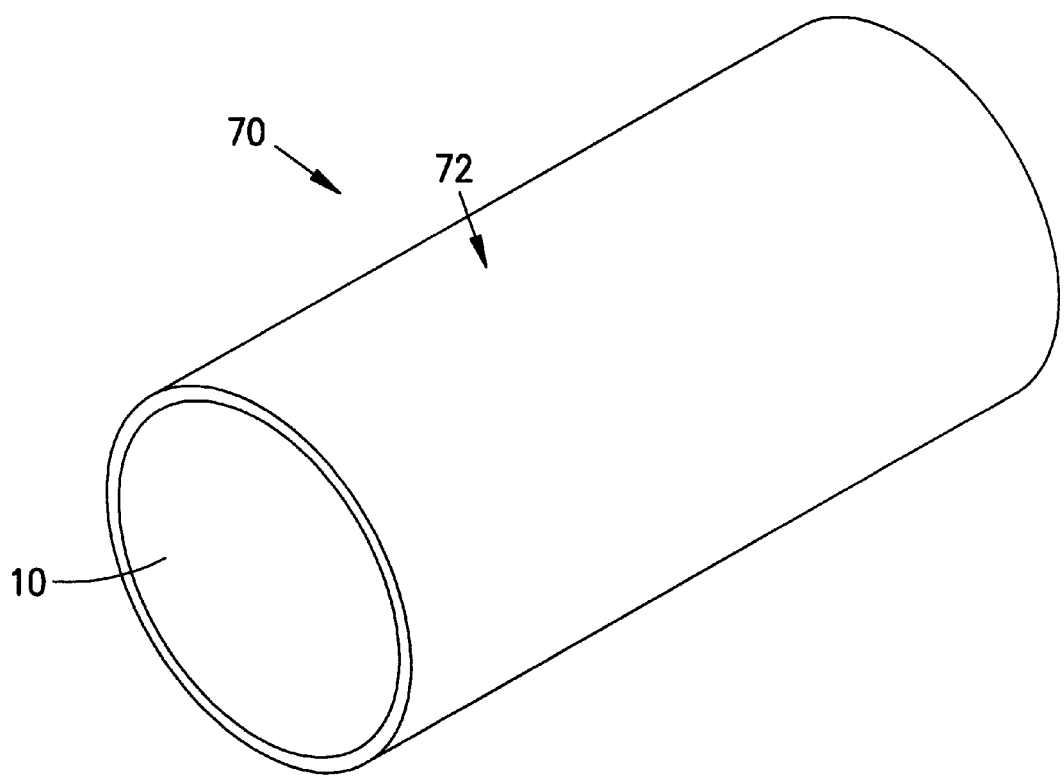
FIG. 7A illustrates an expandable tubular cover embodiment of the tacky layer-polymeric cover of the present invention.
Figure 7B:
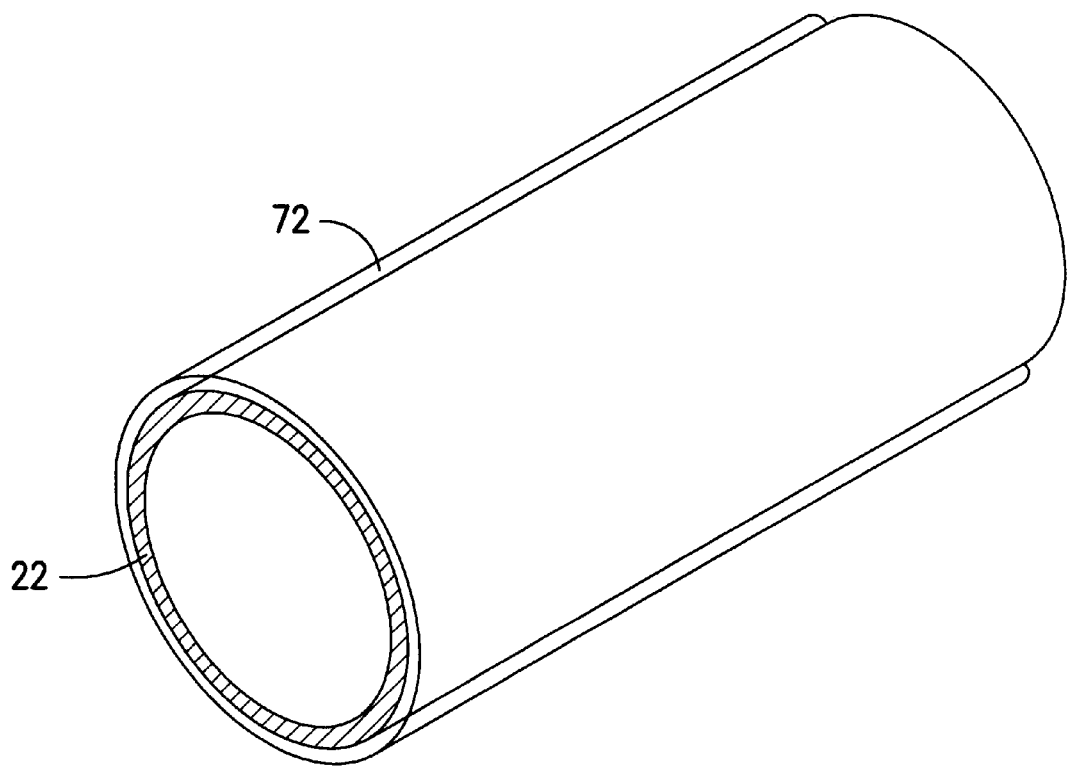
FIG. 7B illustrates a stent-tacky layer-expandable tubular cover embodiment of the present invention.

Another embodiment of the present invention, illustrated generally at 70 in FIG. 7A includes a tubular, expandable main body 72, which is coated with the tacky layer 10 of the present invention on an inner annular surface. A stent 22 is positioned within the tubular, expandable main body 72, as is shown in FIG. 7B.

In another embodiment of the present invention, illustrated generally in FIG. 5, the stent is drug loaded so that the stent comprises a stent metal structural member 42 and a planar sheet or film of polymeric material 44. The film of polymeric material 44 has a first end 46 forming a first layer 47 of polymeric material and a second layer 48 overlapping the first end forming a second layer 49 attached to the first layer of the polymeric film 44, preferably by the tacky layer of the present invention 10. Attachment of the first layer 47 of the polymeric film is accomplished by application of the tacky layer 10 of the present invention to the stent metal structural member 42 for some embodiments or to the first polymeric film layer 47 for other embodiments.

In this embodiment, the planar sheet of polymeric material is wrapped circumferentially and cinched tightly as a sleeve on the stent structural member. The tacky layer 10 of the present invention is applied to either the stent or to an internal surface 47 of the sleeve prior to attachment. The internal surface contacts the stent structural member 42.

Figure 6:
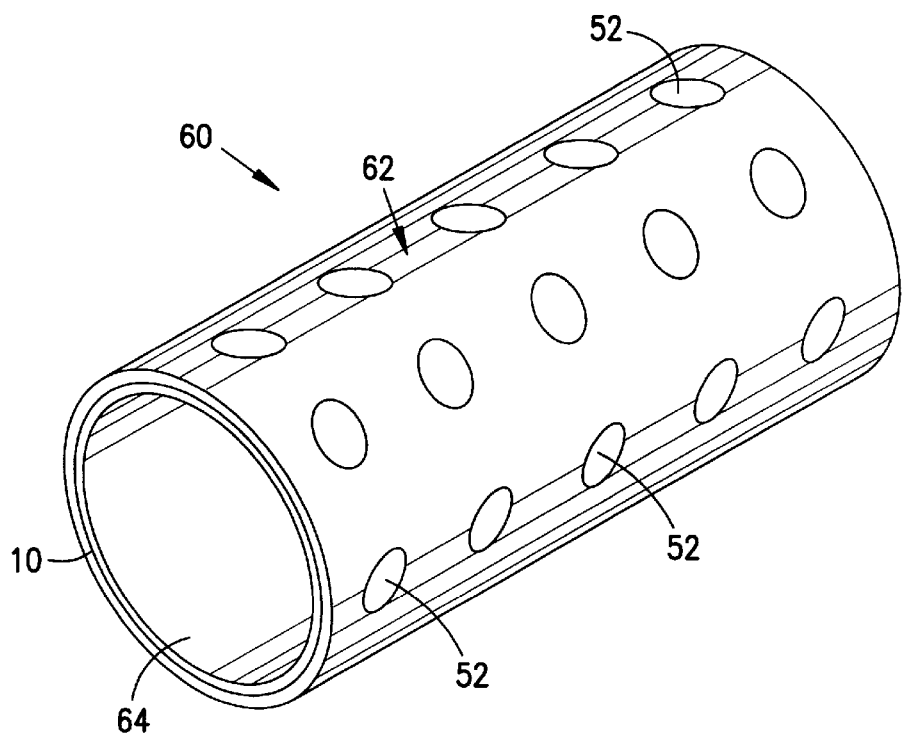
FIG. 6 illustrates a perspective view of one embodiment of a stent-tacky layer-polymeric cover wherein the polymeric cover is a sleeve and is drug loaded.
Figure 6A:
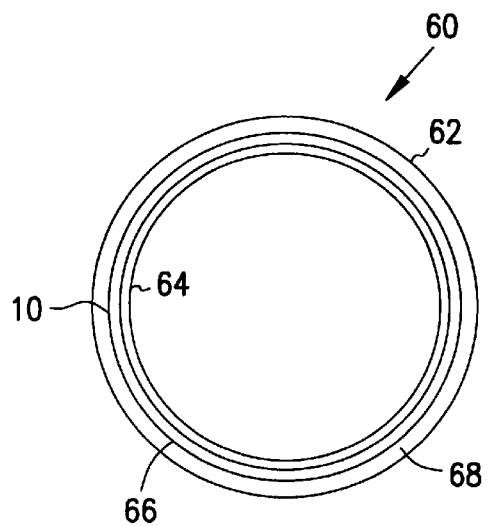
FIG. 6A illustrates the stent-tacky layer-polymeric cover of FIG. 6 in an unexpanded position.
Figure 6B:
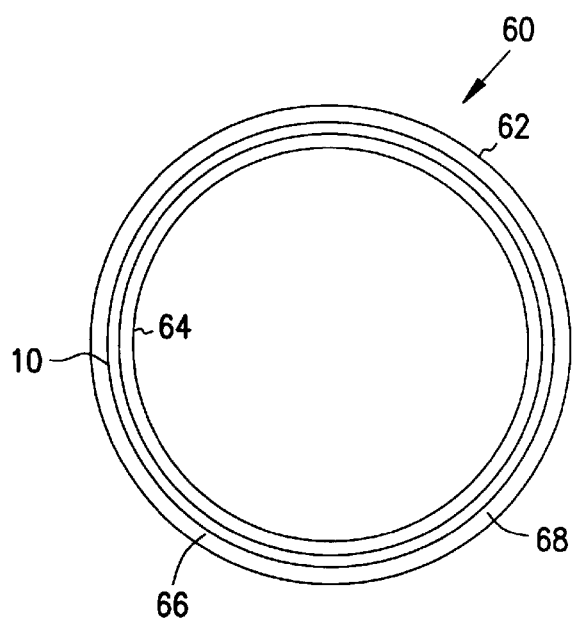
FIG. 6B illustrates the stent-tacky layer-polymeric cover of FIG. 6 in an expanded position.

For some stent embodiments, illustrated in FIGS. 5 and 6, the polymeric material defines apertures such as are shown at 52, formed within the polymeric material. The apertures 52 impart a porousness to the polymeric material and allow blood flow through the stent structural member to a vessel wall such as for oxygenation and nutrient exchange to the vessel wall in order to prevent a decreased surface area for purposes of reducing thrombogenicity. The apertures 52 improve flexibility of the polymeric material allowing the stent segment to be more easily rolled and coiled during expansion of the stent structural member and also facilitate the process of cell growth over the surface of the stent In another embodiment, illustrated at 60 in FIGS. 6, 6A and 6B, a polymeric material is formed as a seamless tube or sleeve 62 that fits tightly around an unexpanded stent structural member 64, shown in cross-section in FIG. 6A. The seamless polymeric tube 62 is adhered to the stent 64 by the tacky layer 10 of the present invention 10, which is applied to the stent structural member 64. The sleeve 62, tacky layer 10 and structural member 64 are expandable to an expanded configuration, shown in cross-section in FIG. 6B. The sleeve 62 includes an inner layer 66 and an outer layer 68 that overlays the inner layer 66. The outer layer 68 is loaded with drugs after adherence to the stent structural member 64.

A primary function of the outer layer 68 of the sheet or sleeve of polymeric material is to deliver therapeutic drugs, such as drugs to help thrombosis and/or restenosis. The inner layer 66 of polymeric material is selected from a group of polymers that include thermoplastic and elastomeric polymers so that the polymeric film can stretch or deform radially when the structural member 62 is expanded.

The planar sheet of polymeric material has a surface that defines a plurality of apertures 52 of various sizes and shapes to promote rapid endothelialization similar to the embodiment illustrated in FIG. 4. The stent is mounted on a balloon dilatation catheter for deployment of the stent in the vasculature of a patient.

In each of these embodiments, the stent structural member is implantable within a vessel in a contracted state and is expandable to maintain patency of the vessel and to allow fluid flow through the vessel. The metal structural member can, for example, be formed from a metal selected from a group of metals that includes stainless steel, MP35N, elastonite (nitinol), tantalum, gold-titanium alloy, platinum-radium alloy, gold and magnesium although the stent structural member is also formable of suitable non-metallic materials. MP35N and MP20N are trade names for alloys of cobalt, nickel, chromium and molybdenum available from Standard Pressed Steel Co., of Jenkintown, Pa. MP35N consists of 35% cobalt, 35% nickel. MP20N consists of 50% cobalt, 50% molybdenum.

The polymeric material is selected from thermoplastic and elastomeric polymers. In one embodiment, the polymeric material is a material available under the trade name (C-flex from Concept Polymer Technologies of Largo, Fla.). In another embodiment, the polymeric material is ethylene vinyl acetate (EVA). In another currently available embodiment, the polymeric material is a material available under the trade name Biospan. Other suitable polymeric materials include latexes, urethanes, polysiloxanes, and modified styrene-ethylene/butylene styrene block copolymers (SEBS), expandable polytetrafluoroethylene (PTFE) and their associated families as well as elastomeric, bioabsorbable linear aliphatic polyesters.

The polymeric material is used to make a layer that has a thickness within a range of about 0.002 to about 0.020 inches. For some embodiments, the polymeric material is bioabsorbable and is loaded or coated with a therapeutic agent or drug, including, but not limited to antiplatelets, antithrombins, cytostatic and antiproliferative agents, for example, to reduce or to prevent restenosis in the vessel being treated. A therapeutic agent or a drug is preferably selected from the group of therapeutic agents or drugs that include sodium heparin, low molecular weight heparin, hirudin, argatrobin, forskolin, vapiprost, prostacyclin and prostacyclin analogues, dextran, D-phe-pro-arg-chloromethylketone, dipyridamole, glycoprotein, IIB/IIIA platelet membrane receptor antibody, recombinant hirudin, thrombin inhibitor, angiopeptin, angiotensin converting enzyme inhibitors, such as captopril available from Squibb; Cilazapril available from Hoffman-La Roche; or Lisinopril available from Merck, calcium channel blockers, colchicine, fibroblast growth factor antagonists, fish oil, omega 3-fatty acid, histamine antagonists, HMG-CoA reductase inhibitor, methotrexate, monoclonal antibodies, nitroprussid, phosphodiesterase inhibitors, prostaglandin inhibitor, seramin, serotonini blockers, steroids, thioprotease inhibitors, triazolo pyrimidine and PDFG antagonists, alpha-interferon and genetically engineered epithelial cells and combinations thereof. While the foregoing therapeutic agents have been used to prevent or treat restenosis and thrombosis, they are provided by way of example and are not meant to be limiting, as other therapeutic drugs may be developed which are equally applicable for use with the present invention.

While particular forms of the invention have been illustrated and described, various modifications can be made without departing from the spirit and scope of the invention. Accordingly, it is not intended that the invention be limited except by the appended claims.

What is claimed is:

1. A stent comprising:

a structural support;

a polymeric film or sheet or tube that overlays the structural support; and a tacky portion that adheres the polymeric film or sheet or tube to the structural support wherein the tacky portion comprises sugar, starch, polyvinylalcohol or degradation products of these materials.

2. The stent of claim 1 wherein the structural support and the polymeric film and the tacky portion are expandable.

3. The stent of claim 1 wherein the tacky portion comprises sugar or starch or polyvinylalcohol or mixtures of sugar and polyvinylalcohol or starch and polyvinyacohol.

4. The stent of claim 1 wherein the structural support is coiled.

5. The stent of claim 1 wherein the structural support is tubular.

6. The stent of claim 5 wherein the tubular structural support defines apertures.

7. The stent of claim 5 wherein the tubular structural support defines slits.

8. The stent of claim 5 wherein the tubular structural support is coated.

9. The stent of claim 1 wherein the polymeric film comprises one or more of ethylene vinyl acetate, latexes, urethanes, polytetrafluoroethylene, polysiloxanes, and modified styrene-ethylene/butylene styrene block copolymers.

10. The stent of claim 1 wherein the polymeric film comprises one or more drugs.

11. The stent of claim 1 wherein the polymeric film defines apertures.

12. The stent of claim 1 wherein the polymeric film is an expandable sleeve.

13. A stent assembly, comprising:

a structural member;

a polymeric sleeve; and a tacky portion that adheres the sleeve to the structural member, the tacky portion comprising one or more of a sugar, a starch, polyvinylalcohol or a mixture of these materials.

14. The stent assembly of claim 13 wherein the structural member and polymeric sleeve are expandable.

15. The stent assembly of claim 13 wherein the polymeric sleeve contains drugs.

16. A stent assembly, comprising:

a structural member;

a polymeric sheet; and a tacky portion that adheres the polymeric sheet to the structural member and that adheres one end of the sheet to the sheet to form a sheet tube, the tacky portion comprising sugar, starch, polyvinylalcohol or a mixture of these materials.

17. The stent assembly of claim 16 wherein the structural member and the polymeric sheet tube are expandable.

18. The stent assembly of claim 16 wherein the polymeric sheet contains drugs.

* * * * *